Figure 1:
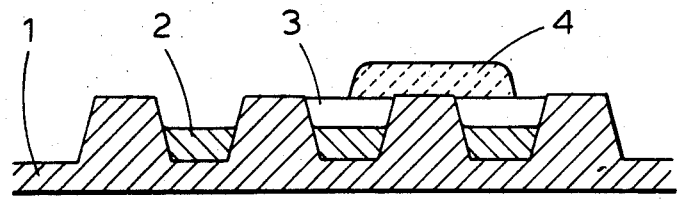

United States Patent [19]

Rawlings et al.

[11] Patent Number: 4,657,006
[45] Date of Patent: Apr. 14, 1987

[54] SURGICAL DRESSING

[75] Inventors: David A. Rawlings, Stansted Mountfitchet; William D. Potter, Bishops Stortford, both of United Kingdom

[73] Assignee: Smith and Nephew Associated Companies p.l.c., England

[21] Appl. No.: 874,057

[22] Filed: Jun. 13, 1986

Related U.S. Application Data

[63] Continuation of Ser. No. 535,614, Sep. 26, 1983, abandoned.

[30] Foreign Application Priority Data

Oct. 2, 1982 [GB] United Kingdom ................ 8228224
Dec. 22, 1982 [GB] United Kingdom ................ 8236411
Jul. 26, 1983 [GB] United Kingdom ................ 8320041

[51] Int. Cl.$^4$ ............................................. A61L 15/00
[52] U.S. Cl. ..................................... 128/156; 604/307
[58] Field of Search ........................ 128/156; 604/307

[56] References Cited

U.S. PATENT DOCUMENTS

| | | | |
|---|---|---|---|
| 1,956,695 | 5/1934 | Reinitz | 128/155 |
| 2,647,100 | 7/1953 | Salditt | 128/156 |
| 2,871,218 | 1/1959 | Schollenberger | 260/45.4 |
| 2,949,443 | 8/1960 | Merriam et al. | 128/156 |
| 3,121,021 | 2/1964 | Copeland | 117/122 |
| 3,483,018 | 12/1969 | Waldman | 128/156 |
| 3,520,949 | 7/1970 | Shepherd et al. | 264/183 |
| 3,526,224 | 9/1970 | Potts | 128/156 |
| 3,579,628 | 5/1971 | Gander et al. | 424/81 |
| 3,645,835 | 2/1972 | Hodgson | 128/156 |
| 3,658,065 | 4/1972 | Hirsch | 128/156 |
| 3,709,221 | 1/1973 | Riely | 128/156 |
| 3,821,136 | 6/1974 | Hudgin et al. | 260/9 |
| 3,822,238 | 7/1974 | Blair et al. | 3/1 |
| 3,903,882 | 9/1975 | Augurt | 128/156 |
| 3,975,350 | 8/1976 | Hudgin et al. | 3/1.91 |
| 4,061,618 | 12/1977 | Stanley et al. | 260/29.3 |
| 4,156,066 | 5/1979 | Gould | 428/425 |
| 4,156,067 | 5/1979 | Gould | 128/156 |
| 4,219,019 | 8/1980 | Coates | 128/156 |
| 4,231,357 | 11/1980 | Hessner | 128/156 |
| 4,289,125 | 9/1981 | Hung | 128/156 |
| 4,308,623 | 1/1982 | Voorhees | 128/151 |
| 4,340,043 | 7/1982 | Seymour | 128/132 D |
| 4,413,621 | 11/1983 | McCracken et al. | 128/156 |
| 4,414,970 | 11/1983 | Berry | 128/156 |
| 4,452,845 | 6/1984 | Lloyd et al. | 128/156 |
| 4,499,896 | 2/1985 | Heinecke | 128/156 |

FOREIGN PATENT DOCUMENTS

| | | |
|---|---|---|
| 682871 | 3/1964 | Canada . |
| 0006714 | 1/1980 | European Pat. Off. . |
| 0028452 | 5/1981 | European Pat. Off. . |
| 0050035 | 10/1981 | European Pat. Off. . |
| 0045592 | 2/1982 | European Pat. Off. . |
| 0050514 | 4/1982 | European Pat. Off. . |
| 0051935 | 5/1982 | European Pat. Off. . |
| 0059049 | 9/1982 | European Pat. Off. . |
| 0081988 | 6/1983 | European Pat. Off. . |
| 0091800 | 10/1983 | European Pat. Off. . |
| 8303549 | 10/1983 | World Int. Prop O. ........... 128/156 |
| 648733 | 1/1951 | United Kingdom . |
| 761840 | 11/1956 | United Kingdom . |

Primary Examiner—William R. Dixon, Jr.
Assistant Examiner—Steven Capella
Attorney, Agent, or Firm—Jacobs & Jacobs

[57] ABSTRACT

A moisture vapor permeable, adhesive surgical dressing is described which comprises a continuous film of a hydrophilic polymer which has a moisture vapor permeability which is greater when in contact with water than when not in contact with water and which is attached around its edges to a water transmitting film so as to form a sealed portion into which exudate may pass from an exuding wound. The water transmitting film comprises a backing layer and an adhesive layer on the side remote from the continuous film. The adhesive layer is suitable for adhering the dressing to the skin. The water transmitting film allows or is adapted to allow access of water to the film when in contact with water so that when used on an exuding wound the high moisture vapor permeability of the continuous film allows water to evaporate through the dressing and prevents the dressing forming a blister.

The low moisture vapor permeability of the film when not in contact with water makes the dressing suitable for use on non-exuding wounds. Preferably a second water transmitting film is present between the continuous film and the water transmitting layer.

20 Claims, 2 Drawing Figures

SURGICAL DRESSING

CROSS-REFERENCE

This is a continuation of Ser. No. 535,614 filed Sept. 26, 1983, abandoned.

The present invention relates to surgical dressings for use on human bodies, for example on wounds. In particular, this invention relates to a dressing comprising a continuous film and an interrupted film attached thereto, which interrupted film preferably has an adhesive thereon.

During surgery and in other medical situations, it is often necessary to sterilise a site on the body requiring treatment, from which sterile site bacteria are excluded and which site can be observed for as long as required. One way of achieving this is to apply to the site a self-adhesive, conformable, transparent and sterile dressing such as those described in British Patent Specification No. 1 280 631.

One of the dressings described in that specification is now known as Op-Site (Trade Mark) and has been used in relation to burns, donor sites, surgical incisions, intravenous catheters, and the like. The Op-Site, and related, dressings comprise a permeable, pressure-sensitive adhesive material which is overall continuous (i.e., either the backing material or the adhesive or both are continuous). By "continous" herein is meant contains no pores (including micropores) capable of allowing the passage of bacteria.

It is often desirable to allow a wound to heal in its 'moist' state (i.e. covered with a layer of wound exudate) as it is believed that this may accelerate healing. The problems with moist wound healing when the wound is covered with a surgical dressing is that a 'blister' of exudate can form under the dressing which is not only unsightly but also may cause the dressing to leak, thereby defeating the aim of sterility. Such an excess of exudate therefore needs to be removed before a harmful blister forms, but usual methods of aspiration may also destroy the sterility. Also, in moist wound healing, it is not desired to remove all the exudate because a 'dry' wound would result.

The present invention helps solve this problem by providing a surgical dressing, suitable for use on moist wounds on human bodies, which comprises a continuous film having a moisture vapour transmission rate which reversibly increases as the amount of water with which the film is in contact increases, and an interrupted water-permeable film attached to the continuous film.

By describing the continuous film as 'having a moisture vapour transmission rate (MVTR) which reversibly increases as the amount of water with which the film is in contact increases', it is meant that when the whole of the water-contacting surface of the film is in contact with water, the film and hence the dressing shows a constant and reproducible high value for its MVTR. As the water evaporates and is not replaced the area of the surface of the continuous film which is in contact with the water becomes gradually smaller and the MVTR of the dressing decreases accordingly. A point is reached at which no wter is in contact with the film and the MVTR reaches a second constant and reproducible value. The skilled man will recognize that the characteristics of the film may be uniquely defined in terms of these MVTR values.

Hence it is clear that the present invention provides an adhesive surgical dressing suitable for use on moist wounds on human bodies which comprises a continuous film having a moisture vapour permeability of not less than 8000 gm$^{-2}$24 hr$^{-1}$ when in contact with water and not more than 4800 gm$^{-2}$24 hr$^{-1}$ when not in contact with water when measured at 37° C. and 100-10% relative humidity and an interrupted water permeable film laminated thereto which carries an adhesive on its surface remote from the continuous film so that the dressing is adhesive.

A dressing according to this invention has the advantage of allowing water to evaporate rapidly from the wound area in the presence of an excess of exudate at and on the wound but, as the amount of exudate diminishes, so does the rate of evaporation; thereby, the resulting amount of exudate around and on the wound is just enough to keep it moist without causing blistering of the dressing.

Conveniently, and preferably, the interrupted film comprises a backing carrying an adhesive on its surface remote from the continuous film so that the dressing is adhesive to the skin surrounding the wound.

The present invention provides a moisture vapour permeable adhesive surgical dressing characterised in that the dressing comprises a continuous film which has a moisture vapour permeability which is greater when in contact with water than when not in contact with water and which continuous film is attached at least around its edges to a water transmitting film so as to form a sealed portion into which exudate may pass from an exuding wound, said water transmitting film being interrupted in at least the area within the sealed portion and which water transmitting film comprises a backing layer and an adhesive layer on the side remote from the continuous film suitable for adhering the dressing to the skin, whereby the dressing has a high moisture vapour permeability which prevents the dressing forming a blister when used on an exuding wound.

Thus it is clear that in one aspect the present invention provides a moisture vapour permeable, adhesive surgical dressing characterized in that the dressing comprises a continuous film which has a moisture vapour permeability which is greater when in contact with water than when not in contact with water and which continuous film is attached at least around its edges to a water transmitting film so as to form a sealed portion into which exudate may pass from an exuding wound, said water transmitting film being coextensive with the continuous film and being interrupted in the area within the sealed portion and which water transmitting film comprises a backing layer and an adhesive layer on the side remote from the continuous film suitable for adhering the dressing to the skin, whereby the dressing has a high moisture vapour permeability which prevents the dressing forming a blister when used on an exuding wound. The dressing is also suitable for use on non-exuding wounds.

The continuous film suitably has the following moisture vapour permeability (MVP) characteristics which are determinable by a method given in the Examples: MVP is not less than 8000 gm$^{-2}$24 hr$^{-1}$ when in contact with water ('wet MVP') and not more than 4800 gm$^{-2}$24 hr$^{-1}$ when not in contact with water ('dry MVP') measured at 37° C. and 100-10% relative humidity. (RH).

Preferably, the continuous film for use in this invention has a wet MVP of >10000 cm$^{-2}$24 hr$^{-1}$ and, more preferably, of >12000 cm$^{-2}$24 hr$^{-1}$, measured at 37° C. and 100-10% RH.

Preferably the continuous film for use in this invention has a dry MVP of <4000 gm$^{-2}$24 hrs$^{-1}$ and, more preferably, of <3600 gm$^{-2}$24 hr$^{-1}$, measured at 37° C. and 100-10% RH.

The moisture vapour permeabilities of the continuous films will vary with the thickness of the film. In the case of the dry-MVP, the permeability of the film is subject to the known relationship of being inversely proportional to the thickness, that is, if the film thickness is doubled, and permeability is reduced by a factor of 2. In the case of the wet-MVP, the relationship between the thickness and permeability of the film appears to follow no simple formula. In particular the wet-MVP gives a lower value than expected if for example the film thickness is reduced by a factor of 2.

Suitably the dressing of this invention will have a wet-MVP of not less than 2500 gm$^{-2}$24 hr$^{-1}$, more suitably not less than 3000 gm$^{-2}$24 hr$^{-1}$, most suitably not less than 3200 gm$^{-2}$24 hr$^{-1}$ and preferably not less than 4000 gm$^{-2}$24 hr$^{-1}$.

Suitably the dressing of this invention will have a dry-MVP of not more than 2000 mg$^{-2}$24 hr$^{-1}$, more suitably not more than 1500 gm$^{-2}$24 hr$^{-1}$, most suitably not more than 1400 gm$^{-2}$24 hr$^{-1}$ and preferably will have a dry-MVP of not more than 1200 gm$^{-2}$24 hr$^{-1}$.

The material used for the continuous film in this invention will have a sufficiently higher wet-MVP than dry-MVP to produce the desired MVP parameters in the dressing.

When the continuous film is associated with the adhesive interrupted film in the dressing, the MVTR of the dressing when in contact with water or wound exudate will reflect the high value of the continuous film as water will be passing through the openings in the interrupted film and will be lost through the continuous film. However, when the continuous film is not in contact with water the MVTR of the Dressing will reflect the lower MVP of the interrupted film as hereinafter described, otherwise the wound would rapidly dry out and the advantageous moist conditions required for wound healing would be lost.

Polymer materials which are suitable for use as continuous films by possessing the desired enhancement of 'wet-MVP' compared to their 'dry-MVP', are those containing chemical groups generally considered to be hydrophilic. Such groups include hydroxyl, ether, ester, carboxyl, amine, amide and carbonyl groups. Thus suitable materials include hydrophilic polyurethanes, cellulose derivatives, polyether-polyamides, polyamides, crosslinked polyvinyl alcohols and the like.

Most suitably the continuous film will be from 15 microns to 80 microns thick, will more usually be from 20 to 60 microns thick and will preferably be from 22 to 50 microns thick, for example 25, 30 35 or 40 microns thick.

Suitably, also, the continuous film will be formed from a hydrophilic polymer which when hydrated contains up to 90% water, preferably from 5% to 50% of water, more preferably from 10% to 40% of water and favourably from 20 to 30% water, for example 25% water.

A preferred hydrophilic polymer is a hydrophilic polyurethane which when hydrated contains from 10 to 40% water.

In order to enable visual observation of the wound, it is desirable for the continuous film used in this invention to be transparent. This in turn requires that the film should preferbly be capable of being self-supporting, that is sufficiently coherent when wet or dry to be used without recourse to additional support such as a fabric, for example a gauze, net or the like. It has been found that polyether polyurethanes are particularly suitable for use in the formation of such films. Favoured polyether polyurethanes are essentially free of reactive substituents such as hydroxy or carboxy groups. Such polyurethanes for use in this invention include random polymers containing units derived from diolic compounds and di-isocyanates.

The ether units in such hydrophilic polyurethanes for use in this invention may be notionally derivable from ethylene diol and a propylene or butylene diol; that is they will contain $CH_2CH_2O-$ units and $-CH_2CH_2CH_2O-$, $-CH_2CH(CH_3)O-$ or $-CH_2CH_2CH_2CH_2O-$ units. Preferably, the ether units in the polyurethane will contain $-CH_2CH_2O-$ and $-CH_2CH(CH_3)O-$ or $-(CH_2)_4O-$ or mixtures thereof of which poly $-CH_2CH(CH_3)O-$ blocks are preferred. Desirably, the mole ratio of poly(ethylene glycol) to poly[(prop or but)ylene glycol]-derivble blocks present in the hydrophilic polyurethanes varies between 1:1 to 1:30; preferably from 1:2 to 1:10; and more preferably from 1:2.5 to 1:4. The molecular weights of these blocks is suitably from 600 to 6000 and favourably from 900 to 4000, for example 1000 to 2000.

Preferably, such hydrophilic polyurethanes for use in this invention will contain residues of aliphatic diols of up to 10 carbon atoms and more preferably up to 4 carbon atoms (of which ethane diol is preferred) as chain extenders wherein the mole ratio of diol to polyglycol used in the preparation of the polymer is from 3:1 to 1:4; preferably, 5:2 to 1:3; and more preferably from 2:1 to 1:2.

The hydrophilic polyurethane should contain sufficient di-isocyanate residues to produce the water contents set forth above when the film is hydrated.

The hydrophilic polyurethane for use in this invention may contain di-isocyanate residues which may be residues of aromatic or aliphatic di-isocyanates such as 4,4'-diphenylmethane di-isocyanate, toluene di-isocyante, 1,6-hexamethylene di-isocyanate or the like. Favoured di-isocyanates for use in the hydrophilic polyurethane of this invention are 4,4'-dicyclohexylmethane di-isocyanate (which is preferred) and 4,4-diphenylmethyl di-isocyanate.

Less preferably than using aliphatic diol chain extenders, the hydrophilic polyurethane may employ equivalent quantities of aliphatic diamine or aliphatic aminol chain extenders of which ethylene diamine is preferred. Similarly somewhat less preferably than using aliphatic diol chain extenders, the hydrophilic polyurethane may employ an aromatic diamine such as phenylenediamine, benzidine or diaminodiphenylmethane.

Less preferably than using a mixture of poly(ethylene glycol) and poly[(prop or but)ylene glycol] derived blocks, the hydrophilic polyurethane may employ poly(ethylene glycol) derived blocks alone together with a higher proportion of chain extender and di-isocyanate.

More preferably, the hydrophilic polyurethane used in a dressing of this invention is essentially a single type of polymer (a product of the polymerisation of the same materials) although blends may be employed to form the hydrophilic polyurethane if desired.

Further favoured materials are polyether-polyamide block copolymers whose preparation and properties have for example been described in British Pat. No. 1473972, French Patent Nos. 1444437 and 2178205 and U.S. Pat. No. 3,839,243. A particularly apt polyether-polyamide block copolymer is known as Pebax 4011 RN 00 (available from ATO Chemical Products (UK) Ltd.). This polymer has a water content of 55% (approx) when hydrated and a 'wet-MVP' of >14000 gm$^{-2}$24 hr$^{-1}$ and a 'dry-MVP' of 18,500 gm$^{-2}$24 hr$^{-1}$ for 70 micron thickness of film at 37° C. and a relative humidity of 100-10%.

A further suitable, though less preferred material is a plasticized regenerated cellulose film such as cellulose acetate. A suitable film is Rayophene 325P (available from British Sidac Ltd.). This film has a 'wet-MVP' of >14,000 gm$^{-2}$24 hr$^{-1}$ and a 'dry-MVP' of 4100 gm$^{-2}$24 hr$^{-1}$ for a 30 micron film when measured at 37° C. and 100-10% relative humidity.

A further suitable, though less preferred material is a polyvinyl alcohol which has been cross-linked, usually by means of heat, to form an insoluble but water absorbent film. A suitable polyvinyl alcohol is available as Polyviol W28/20 (Trade Mark, available from Wacker-Chemie GmbH). The polymer may be cast into a film from aqueous solution, dried and cross-linked using heat for example by autoclaving. This film has a 'wet-MVP' of >13,000 gm$^{-2}$24 hr$^{-1}$ and a 'dry-MVP' of 4800 (approx.) gm$^{-2}$24 hr$^{-1}$ for a 37.5 micron film when measured at 37° C. and 100% to 10% relative humidity difference.

It is preferred that the continuous film is formed from a synthetic polymer rather than a natural polymer or a derivative thereof. The dressing of which the continuous film forms part should conform readily to the body area to which it is applied and should also be elastic. Such dressings have the advantage of adhering securely to the body by following the body contours and allowing the body to move without dislodging the dressing. Synthetic polymers are more conformable and elastic than natural polymers which tend to be stiff, inelastic and generally nonconformable. Synthetic polymers are therefore preferred for the continuous film.

Interrupted films for use in this invention will be made from elastic or non-elastic moisture vapour impermeble or permeable, conformable natural or synthetic polymers but will be in a form which allows or is adapted to allow the passage of liquid water from the wound to the continuous film. Aptly the interrupted films will be made from elastic, conformable moisture vapour impermeable or permeable synthetic polymers. The materials comprising the interrupted film do not need to exhibit the different wet and dry moisture vapour permeability of the continuous film, although some difference may be exhibited in the moisture vapour permeable films.

When used herein the term interrupted film means a film which allows transmission of water through the film, that is a water transmitting film. Such films will allow transmission of water by being in the form of a net, woven or non-woven fabric or be adapted to allow transmission of water by being a continuous film which has been interrupted by perforation, formation of slits or the like.

The materials which comprise the interrupted film need not be permeable per se, but may be adapted to allow passage of water from the wound site to the continuous film, by being interrupted, for example being perforated over the area which is to cover the wound site. If the interrupted film is comprised of material which is impermeable it is advisable to have this film coextensive with the continuous film and not to have this material covering non-wound areas in an uninterrupted state, otherwise maceration of the skin will result. If such a material is used in those dressings in which the interrupted area is surrounded by an area which is to be used for adhering the dressing to the skin, then the interrupted film will be inerrupted in this further area also. In this case the adhesive layer may be similarly interrupted, for example perforated, porous, microporous or pattern spread or in the form of a continuous layer. If the adhesive is present as a continuous layer the dressing will continue to be impermeable to bacteria and to liquid water.

However it is particularly advantageous if the materials which comprise the interrupted layer are permeable such that their moisture vapour permeabilities are greater than 300 gm$^{-2}$24 hr$^{-1}$, and preferably greater than 500 gm$^{-2}$24 hr$^{-1}$ when measured at 37° C. and 100% to 10% relative humidity difference when measured by the Payne Cup method. Suitable materials therefore include backing materials which are continuous or microporous films coated with a moisture vapour permeable adhesive or pattern spread or discontinuous spread with a conventional surgical adhesive by a method described in for example British Pat. No. 819,635. Therefore it is clear that there may be two areas in the dressing with different requirements: one for covering the wound and one for covering the skin.

Materials which are suitable for forming the backing layer of the interrupted film and which are permeable to moisture vapour include those which are described in British Patent Specification No. 1280631 as backing materials, in European Patent Application No. 51935 and in U.K. Application No. 2081721 as polyurethane blend films, each patent is incorporated herein by cross-reference. A preferred backing layer is a polyurethane which is known as an Estane (available from B. F. Goodrich). Suitable Estanes include Estanes 5702, 5701 and 581201. A second preferred backing layer described in European Application No. 51935 is a polyester elastomer which is known as a Hytrel (Trade Mark, available from E. J. duPont de Namours & Co., Wilmington, Del.). Suitable Hytrels include Hytrel 4056. A third preferred backing layer comprises a blend of a linear polyurethane (60 parts by weight of Estane 580201) and a high impact polystyrene (40 parts by weight of compound ref. 6MW available from R. H. Cole Limited).

Materials which are suitable for forming the backing layer of the interrupted film and which are impermeable to moisture vapour include polyolefin films, such as polyethylene, polybutadiene, polyolefin copolymers such as ethylene-vinyl acetate copolymers, polyester and the like.

Other materials which are permeable to moisture vapour include conformable microporous films which have a moisture vapour transmission rate of 300 to 5000 grams, preferably 500 to 4000 gm$^{-2}$24 hr$^{-1}$ at 37.5° C. at 100% to 10% relative humidity difference. Suitable microporous films have an average pore diameter of less than 2 microns, desirably less than 0.6 microns and preferably less than 0.1 microns. Suitable polymers include plasticised polyvinyl chloride, elastomers of polyurethane and ethylene-vinyl acetate copolymer elastomers. A particularly favoured polymer is plasticised polyvinyl chloride.

Suitably the interrupted film will have a thickness of up to 150 microns, more suitably will be from 15 to 100 microns thick, most suitably will be 20 to 75 microns thick and preferably 25 to 40 microns thick, for example 25 microns, 30 microns, 35 microns or 40 microns.

The interrupted films of this invention will carry on the side remote from the continuous film an adhesive layer making the dressing adhesive at least over the area of the skin surrounding the wound and hence the adhesive interrupted film must be moisture vapour permeable to avoid damage or maceration to the skin surrounding the wound if the dressing is to be adhered to this surrounding skin. The adhesive must be compatible with the wound, that is it must not adhere to it. Suitable adhesives will be synthetic polymers or mixtures thereof. Such adhesives may be selected from those described in British Patent Specification No. 1,280,631 and European Patent Application No. 35399, both of which are incorporated herein by reference. Preferred adhesives are those having MVP's such that the adhesive interrupted layer has a MVP>300 gm$^{-2}$24 hr$^{-1}$, more preferably >500 gm$^{-2}$24 hr$^{-1}$ when measured at 37° C. and 100-10% relative humidity. Suitable adhesives are those formed from acrylate ester copolymers or polyvinyl ethyl ethers. If desired such adhesives may incorporate an antibacterial agent.

A preferred pressure sensitive adhesive comprises a blend of high and low viscosity polyvinyl ethyl ethers in particular adhesive composition A disclosed in British Patent Specification No. 1280631. Other preferred pressure sensitive adhesives comprise copolymers of acrylate ester with acrylic acid for example as disclosed in European Patent Application No. 35399, and in particular a copolymer of 47 parts by weight of butyl acrylate, 47 parts by weight of 2-ethyl-hexyl acrylate and 6 parts by weight of acrylic acid with an intrinsic viscosity of at least 1.9 dl/g polymerised in acetone according to the general method given in the above European Application.

Suitably the adhesive is usually employed at a mass weight per unit area of 20 to 80 gm$^{-2}$, more suitably at 20 to 45 gm$^{-2}$ and preferably at 25 to 35 gm$^{-2}$, for example 29 gm$^{-2}$, 32 gm$^{-2}$.

From the above it is clear therefore that a preferred adhesive interrupted film comprises the backing material and adhesive which has been found suitable for use in the wound dressing known as Op-Site. It will be understood however, that although the backing material and/or the adhesives themselves or its self may be continuous as described in British Pat. No. 1280631, when used here it is interrupted at least over the wound area. By interrupted herein is meant that the film is not continuous for all its length and breadth over the wound area.

In a first aspect, a particularly preferred adhesive interrupted film for use in this invention may be simply described as the continuous film used in the Op-Site wound dressing which has been interrupted for example by perforation, at least in the area to be over the wound. These perforations, for example circular holes, will allow the passage of liquid water and normally will be visible to the naked eye and may measure 0.1 to 2.5 mm for example 1.5 mm in diameter. They result in the film being interrupted. The holes will be spaced from 0.5 to 2.5 cm apart, for example 1 cm. Conveniently the holes will be arranged in a grid pattern which defines a wound covering area and the area over which the continuous film will be sealed. Aptly the pattern of holes will be placed centrally in the dressing thereby leaving an adhesive margin of continuous backing layer and adhesive which may be adhered to the skin around the wound thereby reducing the risk of the wound becoming infected.

Alternatively the film may be interrupted by the presence of slits. The slits may be from 0.3 to 1.5 cm in length and be spaced from 0.3 to 1.5 cm apart. The slits may be straight, arcuate or in the form of two slits at right angles. It is preferred if the slits are in the form of single straight slits and that they are arranged in parallel lines over the area which is to be applied to the wound.

In a further aspect therefore the present invention provides a moisture vapour permeable, adhesive, surgical dressing characterised in that the dressing comprises a continuous film which has a moisture vapour permeability which is greater when in contact with water than when not in contact with water and which continuous film is attached at least around its edges to a first water transmitting film so as to form a sealed portion into which exudate may pass from an exuding wound, said first water transmitting film extending beyond the edges of the continuous film and being interrupted in at least the area within the sealed portion and which water transmitting film comprises a backing layer and an adhesive layer on the side remote from the continuous film suitable for adhering the dressing to the skin whereby the dressing has a high moisture vapour permeability which prevents the dressing forming a blister when used on an exuding wound.

Suitably at least one of the backing layer and adhesive layer is continuous in the area which extends beyond the edges of the continuous film, thereby maintaining the bacteria proof and liquid proof properties of the dressing. Most suitably both the backing layer and the adhesive layer will be continuous. As described hereinbefore if the layers are continuous the combination of layers will have a moisture vapour permeability of greater than 300 gm$^{-2}$24 hr$^{-1}$, more suitably greater than 500 gm$^{-2}$24 hr$^{-1}$ and preferably greater than 700 gm$^{-2}$24 hr$^{-1}$ when measured at 37° C. and 100% to 10% relative humidity difference. Suitably the backing layer will be a moisture vapour permeable material as hereinbefore described and is preferably a polyurethane such as an Estane. Suitably the adhesive layer will be a moisture vapour permeable adhesive layer as hereinbefore described, the adhesive will preferably be an acrylate ester copolymer adhesive.

In a further aspect therefore the present invention provides an adhesive surgical dressing suitable for use on moist wounds on human bodies, which comprises a continuous film having a moisture vapour permeability of not less than 8000 gm$^{-2}$24 hr$^{-1}$ when in contact with water and not more than 4800 gm$^{-2}$24 hr$^{-1}$ when not in contact with water, when measured at 37° C. and 100-10% relative humidity and an interrupted water-permeable film attached thereto which interrupted film comprises a polyurethane film carrying on its surface remote from the continuous film an adhesive layer, both film and adhesive layer being perforated in the region which is to cover the wound with holes of 0.1 to 2.5 mm diameter.

In a second example, a dressing according to this invention may comprise a continuous film to which is bonded a net of interrupted film. Normally the net will be formed from an elastomeric polymer. Suitable polymers include polyurethanes, polybutadienes and the like.

Preferably the nets are formed from polyurethanes, including for example the linear polyether or polyester polyurethanes known as Estanes (Trademark of B. F. Goodrich Corp.). Preferred Estanes are 5702, 5701 and 580201. Suitable polybutadienes include 1,2 polybutadienes which are known as RB810, RB820 and RB830 made by Japan Synthetic Rubber Company. The dressings incorporating the nets will be conformable and elastic.

The apertures in the nets may have any convenient form depending upon the contours of the melt-embossed film into which they are cast, for example square, rectangular, circular or diamond shaped. Suitably the net is in the form of a diamond-shaped repeating pattern, the sides of which diamonds are formed from the backing material of the interrupted film.

In a favoured aspect of the invention the conformable and elastic net is in the form of an integral net. The term integral net means a net in which the strands and junctures are formed integrally during manufacture.

Suitable elastic nets will have a thickness of 0.01 to 2.5 mm, typically 0.01 to 0.75 mm and preferably 0.05 to 0.5 mm.

Suitable nets will have apertures with a dimension of from 0.05 to 4 mm, more aptly from 0.05 to 2.5 mm and preferably from 0.1 to 2.5 mm. Favoured apertured films have 4 to 40 apertures per cm with a dimension of 0.05 to 2.5 mm. Suitable nets may be made as described in European Patent Specification No. 59035 which is incorporated herein by cross-reference.

Normally the net will be attached to the continuous film over the whole of its non-adhesive surface as hereinafter described. However the net may be attached only around its periphery to the continuous film either using an adhesive of the type hereinbefore described, by heat sealing or other conventional sealing means.

The net over the wound area will suitably have 15 to 80% of its area void, more suitably 20 to 65% and preferably 25 to 45% of its area void. The area of the film which is void will depend upon the MVP of the backing and adhesive layers. With high MVP layers the void area will be at the lower range.

Normally the net will carry on its surface remote from the continuous film an adhesive which may or may not be coterminous with the area of the backing material. Suitably the adhesive will cover the strands of the net and be coterminous with it. Suitably the adhesive will be a synthetic polymer adhesive as hereinbefore described.

In a further aspect therefore the present invention provides an adhesive surgical dressing suitable for use on moist wounds on human bodies, which comprises a continuous film having a moisture vapor permeability of not less than 8000 gm$^{-2}$24 hr$^{-1}$ when in contact with water and not more than 4800 gm$^{-2}$24 hr$^{-1}$ when not in contact with water, when measured at 37° C. and 100-10% relative humidity and an interrupted water-permeable film attached thereto which interrupted film comprises a net carrying on its surface remote from the continuous film an adhesive layer.

The continuous film will be attached to the interrupted film on the latters' non-adhesive side. This attachment may be achieved by heat sealing, with an adhesive, by welding or the like. The attachment may be made at several points across the interrupted film but will be at least around the edge of the continuous film so as to form a sealed portion into which wound exudate will pass from the wound through the interruptions of the interrupted film. The exudate is thereby brought into contact with the continuous film for water to evaporate from the outer surface of this film. The sealed portion may be subdivided by having as well as the seal around the edge of the continuous film, a pattern of other seals which could for example be such as to give a quilted effect or a grid effect. As described hereinbefore it is not necessary for the continuous film to cover the whole area of the interrupted film provided it covers at least the area which will be over the wound. It is preferred that the attachment is by a heat seal.

In some dressings in using a certain combination of materials for the continuous film and the interrupted film, it is not possible to form a heat seal between them. In such cases an adhesive layer is provided at least at the edges of the continuous film so that it may be adhered to the interrupted film to produce the sealed portion described above. Aptly the adhesive used will be an acrylate ester copolymer adhesive or a polyvinyl ethyl ether adhesive as hereinbefore described. Alternatively the films may be adhered by means of a double sided adhesive tape of the appropriate dimensions to provide a sealing means around the edge of the continuous film.

In a further aspect of the present invention an intermediate layer is provided between the non-adhesive surface of the interrupted film and the continuous layer. The intermediate layer will be water transmitting so as not to prevent the passage of water from the wound to the continuous film. The presence of the intermediate layer may in certain cases aid the manufacture of the dressing by preventing unwanted adherency of the continuous film to the interrupted film during for example, the sterilisation process. The presence of the intermediate layer has further advantages in that it improves the handleability of the dressing and it may slow down the rate of the evaporation of the moisture vapour from the surface of the continuous film which reduces the risk that the wound might dry out and stick to the dressing particularly around the apertures in the interrupted film. The intermediate layer may also carry a medicament which is released to the wound area in use. Suitably the medicament will be an antimicrobial agent.

Materials suitable for forming the intermediate layer include woven and non-woven fabrics, nets, perforated films, hydrogels or hydrophilic polymers and the like which are water permeable. Aptly the intermediate layer is a non-woven fabric or a perforated film or an integral net. Preferably the layer is a non-woven fabric. Generally suitable non-woven fabrics will be formed from hydrophobic polymers such as polyolefins. Preferred non-woven fabrics include a spun bonded polypropylene fabric known as Novelin (Trade Mark, available from J. W. Suominen). In the manufacture of the dressings a piece of the non-woven fabric may be placed over the interrupted area of the interrupted film, the continuous film placed on top of the non-woven fabric and all three layers sealed together around their edges or the continuous film may be simply only sealed to the interrupted film. It is preferred that all three films are sealed.

Films, which when perforated, are suitable for use as an intermediate layer include polyolefin films and polyester film such as Melinex (Trade Mark, available from I.C.I. plc). Aptly these intermediate layers are perforated in a similar manner to the interrupted film as described hereinbefore, that is they are perforated with holes or slits. Surprisingly it has been found that it is advantageous to maintaining the moistness of the wound and to the progress of wound healing if the holes or slits in the interrupted layer are not in register with the holes or slits in the intermediate layer.

Aptly when an intermediate layer is present, this layer is also transparent so that the progress of wound healing may be observed. However, in the case where the layer is a non-woven fabric the fabric may not be transparent, so the centre of this layer may be removed prior to sealing between the continuous film and the interrupted film so that the wound may still be observed.

When the intermediate layer of water transmitting material is in the form of a polymeric film then it will have a thickness similar to that used for the interrupted film that is up to 150 microns. If the intermediate layer is a non-woven or woven fabric then the layer tends to be thicker.

Thus in a further aspect the present invention provides an adhesive surgical dressing suitable for use on moist wounds on human bodies, which comprises a continuous film having a moisture vapour permeability of not less than 8000 gm$^{-2}$24 hr$^{-1}$ when in contact with water and not more than 4800 gm$^{-2}$24 hr$^{-1}$ when not in contact with water, when measured at 37° C. and 100% to 10% relative humidity difference, an interrupted water-permeable film sealed thereto which interrupted film comprises a backing layer carrying on its surface remote from the continuous film an adhesive layer and present between the non-adhesive side of the interrupted film and the continuous film an intermediate layer of a water-transmitting material.

Thus in another favoured aspect the present invention provides a moisture vapour permeable adhesive surgical dressing characterised in that the dressing comprises a continuous film which has a moisture vapour permeability which is greater when in contact with water than when not in contact with water and which continuous film is attached at least around its edges to a first water transmitting film so as to form a sealed portion into which exudate may pass from an exuding wound, said first water transmitting film being coextensive with the continuous film and being interrupted in the area within the sealed portion and which first water transmitting film comprises a backing layer and an adhesive layer on the side remote from the continuous film which is suitable for adhering the dressing to the skin and is characterised further in that the dressing has between the continuous film and the non-adhesive side of the first water transmitting film a second water transmitting film; whereby the dressing has a high moisture vapour permeability which prevents the dressing forming a blister when used on an exuding wound.

Aptly the continuous film will have a moisture vapour permeability of not less than 8000 gm$^{-2}$24 hr$^{-1}$ when in contact with water and not more than 4800 gm$^{-2}$24 hr$^{-1}$ when not in contact with water when measured at 37° C. and 100% to 10% relative humidity. Suitable materials are those which have been described hereinbefore. Preferably the continuous film is a hydrophilic polyurethane film.

Aptly the backing layer will be any of the materials described hereinbefore as being suitable for the interrupted layer. Preferably the backing layer will be a polyurethane film.

Aptly the adhesive layer will be an acrylic ester copolymer or polyvinyl ethyl ether adhesive layer as hereinbefore described.

Optionally the interrupted film may also incorporate or may have attached to its surface remote from the continuous film a water-absorbing material such as a hydrogel such as Spenco (Trade Mark) or a hydrophilic foam such as Hypol (Trade Mark) foam. The presence of such a material does not interfere with the escape of excess water but provides a reservoir of exudate which remains.

Optionally also, an intermediate layer may be provided between the continuous and interrupted films. Preferably, of course, this layer is also transparent.

In use, when a dressing, say of the first example above, according to this invention is first put over the wound, the dressing is dry so the interruptions are relatively insignificant as the major area of the wound is covered by the interrupted film and the interruptions are themselves covered by the continuous (e.g. hydrophilic polyurethane) film. As the amount of wound exudate increases, tending to blister-formation, the exudate seeps through the holes, hydrating the hydrophilic polyurethane, the MVP of which increases so the water evaporates. Once the 'blister' has subsided, the MVP of the continuous film decreases, but the wound still remains moist because most of its area is covered by the less permeable (interrupted) film.

Therefore, the present invention provides a method of dressing a wound on an animal body comprising placing over the wound a dressing which dressing comprises, remote from the wound, a continuous film having a moisture vapour transmission rate which reversibly increases as the amount of wound exudate with which it is in contact increases and, next to the wound, an interrupted permeable film attached to the continuous film, and adhering the dressing to the body.

In a further aspect therefore, the present invention provides a method of dressing a wound on an animal body comprising placing over the wound a dressing which comprises, remote from the wound, a continuous film having a moisture vapour transmission rate which reversibly increases as the amount of wound exudate with which it is in contact increases, an intermediate layer comprising a water permeable film and, next to the wound an interrupted permeable film attached to the continuous film, and adhering the dressing to the body.

Preferably, the dressing according to this invention is provided in sterilised form and, when self-adhesive, is adhered to a removable sterile backing sheet and packaged in a bacteria-proof package such as a paper, plastic or aluminium foil pouch. Sterilisation may be achieved in conventional manner, e.g. by use of γ-irradiation, heat or ethylene oxide.

Suitable forms of dressing and removable backing sheet(s) include ones similar to those described in European Patent Specification No. 51-935. Suitable hydrophilic polyurethanes for use include those described in European Patent Specification No. 50035. Suitable nets may be made as described in European Patent Specification No. 59035. These specifications are incorporated herein by cross-reference.

Dressings according to this invention may be prepared by casting a solution of the adhesive in a suitable solvent such as acetone, into the recesses of a melt-embossed polyolefin sheet so that the recesses are only partially filled. The solvent is partially removed and then a syrup containing the backing polymer is cast onto the adhesive layer. After removing the solvents the adhesive and backing polymer should just fill the recesses of the sheet. This forms an adhesive coated net. A solution of the continuous film polymer is then cast onto a silicone release paper. The solvent is then removed and the resultant film is laminated to the net by pressing between rollers are elevated temperature, for example 75° C. A dressing comprising a continuous film bonded to an adhesive net is thereby formed. The adhesive side of the dressing may then be covered with a conventional release paper.

Alternatively the polymer which is to form the backing layer of the interrupted film may be cast onto a silicone release paper from a solution to give a film of the required thickness and weight when the solvent is removed. An adhesive film may be similarly cast on to a release paper. The adhesive film may be transferred to the backing layer by conventional transfer coating means. The combined films may be then formed into the interrupted film by punching holes of the appropriate diameter through the backing and adhesive layers. Alternatively slits of the appropriate length and shape may be cut through the backing layer and adhesive layer using a sharp blade or an array of such blades which give the correct pattern.

The continuous film may be cast from a solution of the appropriate hydrophilic polymer at the required thickness and weight. This film may be heat sealed or adhered around its edges to the non-adhesive side of the interrupted film. In other instances the continuous film may be formed by extrusion of the appropriate polymer to give a film of the required thickness. The continuous film may be sealed using a heated box-section so that the interruptions of the interrupted film fall within the sealed square so formed. Other dressings according to this invention may be prepared by methods known to those skilled in the art.

The following Examples are provided by way of illustration of this invention. The hydrophilic polyurethanes may be prepared as described in European Pat. No. 50035.

EXAMPLE 1

Preparation of Surgical Dressing

Referring to FIG. 1, a solution of acrylic adhesive (2) in acetone (solids content 35%) was cast into the recesses of a 15 cm wide melt-embossed polypropylene sheet (1) with a 'squeegee' spreader such that the recesses were only partially filled. The sheet had a melt embossed pattern of 4 per cm raised areas in diagonal rows of square truncated pyramids 2 mm wide at their base and 0.45 mm high with sides sloping to a conical angle of 70° C.

After partially removing the solvent for the acrylic adhesive, a polyurethane syrup comprising 100 parts of Estane 5714F (B. F. Goodrich Ltd.), 5 parts of Gasil 23 fine silica (Crossfield Chemical Ltd.), 240 parts of tetrahydrofuran and 160 parts of acetone was cast into the recesses of the embossed sheet on top of the adhesive. After removal of all the solvent the polyurethane formed a net (3) which together with the adhesive, filled the recesses in the sheet.

A solution of hydrophilic polyurethane, having a potential water content of 85% when hydrated, in IMS (15% solids) was cast onto silicone release paper using a spreading box with a 0.01" gap. After removal of the solvent, the resultant film was laminated to the polyurethane net by pressing between rollers at 75° C.

EXAMPLE 2

Preparation of Surgical Dressing

Figure 2:
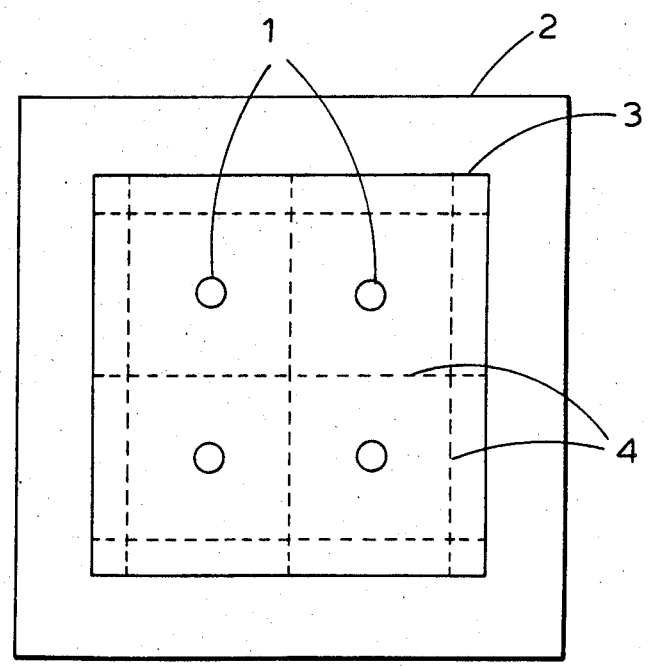

The polyurethane of Example 1 was cast from the solvent to give a film at a weight of 30 gsm on a silicone release paper. To this film was laminated by transfer coating a film of acrylic adhesive also spread at a weight of 30 gsm. After effecting the transfer, the laminate was trimmed to give a 90 mm square dressing. Referring to FIG. 2, four holes, 1.5 mm diameter, centrally punched at 25 mm intervals in the polyurethane-adhesive laminate (2). To the non-adhesive side of laminate (2) was heat sealed a film (3) by hydrophilic polyurethane at a weight of 30 gms and of potential water content of 25%.

Alternatively, a 25 mm box section may be heated to 110° C. and used end-on to seal along lines 4.

A piece of perforated polyurethane film was covered by hydrophilic polyurethane of potential water content 25% using the method described above. This was clamped over a piece of hydrated Spenco (Trade Mark) hydrogel in a 2¼" disc. Approximately 1.5 ml of water was injected through a hole in the disc after which the hole was sealed. The whole was weighed and placed on a hot plate at 37° C. Weighing at 0.5 hr. intervals found the moisture vapour permeability to vary as follows:

| Time (Hrs) | MVP $gm^{-2} 24\ hr^{-1}$ |
| --- | --- |
| 0.5 | 8270 |
| 1.0 | 14570 |
| 1.5 | 9810 |
| 2.0 | 3340 |
| 2.5 | 1480 |
| 3.5 | 890 |
| 4.0 | 650 |
| 4.5 | 610 |
| 5.0 | 640 |
| 6.0 | 590 |
| 6.5 | 560 |
| 7.0 | 630 |
| 23.5 | 530 |

At the end of this time the Spenco hydrogel was removed from the assembly and found to be still moist.

EXAMPLE 3

Preparation of Surgical Dressing

By using the method of Example 2, a dressing was prepared which had the following weights of components: acrylic adhesive film, 50 gsm, polyurethane film 25 gsm and a hydrophilic polyurethane of potential water content 25%, 15 gsm and 15 microns thick.

EXAMPLE 4

Preparation of Surgical Dressing

A film of a polyether-polyamide polymer (Pebax 4011) was formed by extrusion so that the resultant film was 50 microns in thickness. This film was then heat sealed to the non-adhesive side of the preforated adhesive-coated polyurethane film described in Example 2 to form a dressing 85 cm square heat sealed around its edges. The perforated film contained eight perforations, each 1.5 mm in diameter arranged in the form of a square around its centre.

The dressing so formed was placed with the adhesive side of polyurethane film facing downwards with the perforations arranged to be over a foam filled recess in a hot plate which was maintained at a surface temperature of 35° C. The recess was circular in shape, having a diameter of 5 cm and a hole in its base allowed fluid to be pumped into the foam from beneath. Horse serum was pumped into the foam at such a rate as to deliver 6.5 ml in 17.5 hours after which the pumping was stopped. The moisture vapour transmission rate from the top of the dressing i.e. after passing through the polyether-polyamide film was measured using a Servo-Med Evaporimeter EP1 (available from Servo-Med AB of Stockholm, Sweden) placed adjacent to the top of the dressing. The rate was measured from when the serum ceased to be delivered to the foam and at given intervals subsequent thereto. The results are shown below:

| Time after cessation of pumping (hr) | Moisture vapour transmission rate $gm^{-2}24\ hr^{-1}$ |
|---|---|
| 0 | 3240 |
| ½ | 3360 |
| 1 | 768 |
| 2 | 912 |
| 3 | 960 |
| 5 | 720 |
| 17 | 504 |

The rate of delivery of horse serum to the foam was chosen so as to approximate the amount of wound exudate which might be expected from a wound over a similar 17.5 hour period. The results show the decrease in moisture vapour transmission rate as the amount of serum delivered to the foam stops. The foam was still moist at the end of the experiment.

EXAMPLE 5

Preparation of Surgical Dressing

A polyurethane syrup of the composition given in Example 1 was cast to give a film at a weight of 30 gsm on a silicone release paper. To this film was laminated by transfer coating a film of acrylic adhesive also spread at a weight of 30 gsm.

The adhesive used was an acrylic ester copolymer of 47 parts n-butyl acrylate, 47 parts 2-ethylhexyl acrylate and 6 parts acrylic acid which had been polymerised in acetone. The adhesive was spread from acetone solution.

After effecting the transfer, the laminate was cut to form adhesive films 13 cm square. The film had a 'dry' MVP of 560 $gm^{-2}24\ hr^{-1}$ at 37° C. and 100% to 10% relative humidity difference and a 'wet' MVP of 830 $gm^{-2}24\ hr^{-1}$ under the same conditions. The central 8 cm × 8 cm of the adhesive film was perforated by cutting rows of slits, 0.5 cm long, spaced 1 cm apart.

A 15% solution of hydrophilic polyurethane, having a potential water content of 25% when hydrated, in industrial methylated spirits was mixed with 5% fine silica (Gasil 23, Grossfield Chemical Ltd.) and was cast on to silicone release paper to give a film of weight 40 gsm. A 10 cm square of this film was cut and laid on to the non-adhesive polyurethane side of the perforated film and sealed, using an impulse heat sealer, around its edges so that all the slits were covered by the hydrophilic polyurethane film and lay within the heat sealed area. The hydrophilic polyurethane film had a 'dry' MVP of 2200 $gm^{-2}4\ hr^{-1}$ and a 'wet' MVP of >13,000 $gm^{-2}24\ hr^{-1}$ (when measured at 37° C. and 100% to 10% relative humidity difference).

The resulting dressing was tested by applying it, adhesive face down, to an aluminium hot plate maintained at 35° C. The dressing was so adhered as to completely cover a 2 mm deep, 7.5 cm diameter recess in the plate with the area containing the slits. The recess was filled by a disc of polyurethane foam, pre-soaked in horse serum and was provided with a tube through which additional serum could be injected through the foam underneath the dressing. 3 ml of serum were injected to form a blister under the dressing. The serum was observed to immediately penetrate through the slits in the lower polyurethane film layer and to wet the upper hydrophilic polyurethane layer.

The moisture vapour transmission rate from the top of the dressing was measured using a Servo-Med Evaporimeter EP1 (available from Servo Med AB of Stockholm, Sweden) placed adjacent to the top of the dressing. The rate was measured when the 3 ml of serum was injected and at specific intervals thereafter to follow changes in the rate as the volume of excess liquid diminished.

The results were,

| Time after injection (hr.) | Moisture vapour transmission rate $(gm^{-2}24\ hr^{-1})$ |
|---|---|
| 0 | 3,000 |
| 1.5 | 550 |
| 2.5 | 460 |
| 3.5 | 380 |
| 4.0 | 380 |
| 4.5 | 380 |

The results show the decrease in moisture vapour transmission rate as the amount of serum beneath the dressing diminishes. It was observed that at the end of the experiment the foam on the recess was still moist and the dressing had not adhered to any part of the foam.

EXAMPLE 6

Preparation of Surgical Dressing

A film of polyether-polyamide polymer, Pebax 4011 (Trade Mark) was formed by extrusion so that the resultant film was 42 microns in thickness. This film was then heat sealed to the non-adhesive side of an adhesive coated polyurethane film formed as described in Example 5 to form an adhesive dressing which was 13 cm × 8 cm and sealed around its edge. The moisture vapour transmission was measured using the same method as that described in Example 5 with the following results,

| Time after injection (hr.) | Moisture vapour transmission rate $(gm^{-2}24\ hr^{-1})$ |
|---|---|
| 0 | 4,900 |
| 1.5 | 3,890 |
| 2.5 | 2,040 |
| 3.5 | 1,680 |
| 4.0 | 790 |
| 4.5 | 720 |

The results showed that the dressing was suitable for application to wounds.

EXAMPLE 7

Preparation of Surgical Dressing

An adhesive-coated polyurethane film was formed by the method described in Example 5. This film was perforated by punching holes of 1.5 mm diameter at 1 cm spacing over the central 8 cm×8 cm area. A piece of spunbonded polypropylene (Novelin (Trade Mark) available from J. W. Suominen) 9 cm×9 cm was placed over the perforated area of the adhesive-coated film on the non-adhesive side. A piece of hydrophilic polyurethane film, formed as described in Example 5, 10 cm×10 cm was placed over the spun bonded polypropylene layer. The hydrophilic polyurethane was then heat sealed to the polyurethane layer around its edge. The resultant adhesive dressing was tested for its moisture vapour transmission by the method described in Example 5 with the following result.

| Time after injection (hr.) | Moisture vapour transmission rate (gm$^{-2}$24 hr$^{-1}$) |
|---|---|
| 0 | 4,150 |
| 1 | 3,170 |
| 2 | 2,380 |
| 3.5 | 1,180 |
| 4.5 | 700 |
| 5.5 | 670 |
| 6 | 720 |

The results showed that the dressing was suitable for application to an exuding wound.

EXAMPLE 8

Preparation of Surgical Dressing

A film of an elastomeric polyester (Hytrel 4056 (Trade Mark) available from Dupont) approximately 100 microns thick was cold stretched until the thickness was 60 microns. An acrylic adhesive layer was transferred to one surface of the resultant film in a manner described in Example 5. The resultant adhesive film was perforated by punching holes 1.5 mm in diameter at 1 cm spacing over a central 8 cm×8 cm area. This perforated film was laminated to a film of regenerated cellulose acetate (Rayophane 400 PUT 177 (Trade Mark), available from British Sidac Ltd.) using an acrylic adhesive spread around the periphery of the perforated area.

The resultant adhesive dressing was tested for its moisture vapour transmission rate using the method described in Example 5 with the following results,

| Time after injection (hr.) | Moisture vapour transmission rate (gm$^{-2}$24 hr$^{-1}$) |
|---|---|
| 0 | 3,900 |
| 1 | 2,450 |
| 2 | 1,700 |
| 3.5 | 740 |
| 4.5 | 650 |
| 5.5 | 550 |

The results show that this dressing was suitable for application to a wound.

EXAMPLE 9

Preparation of Surgical Dressing

A film of syndiotactic 1, 2 polybutadiene (JSR RB830 available from Japanese Synthetic Rubber Company) was formed by extrusion. The film was 150 microns in thickness. This was transfer coated with an acrylic adhesive. A Central area 8 cm×8 cm was perforated by forming slits, 0.5 cm in length and 1 cm apart. The perforated area on the non-adhesive side was covered by a piece of spun bonded polypropylene. A film of polyether-polyamide polymer was formed by extrusion to give a film 42 microns thickness which was then heat sealed around its periphery to the perforated polybutadiene film, to form an adhesive dressing with a spun bonded polypropylene intermediate layer. This dressing was tested for moisture vapour transmission rate by the method described in Example 5 with the following results,

| Time after injection (hr.) | Moisture vapour transmission rate (gm$^{-2}$24 hr$^{-1}$) |
|---|---|
| 0 | 4,900 |
| 1.5 | 670 |
| 2 | 580 |
| 6 | 530 |

The results showed that this dressing was suitable as a wound dressing.

EXAMPLE 10

Preparation of Surgical Dressing

A film of an ethylene-vinyl acetate copolymer containing 24% vinyl acetate (EVA 24-03 available from I.C.I. Plastics) was formed by extrusion to a thickness of 25 microns. The film was then transfer coated with an acrylic adhesive. The adhesive-coated film was then perforated with holes 1.5 mm in diameter spaced 1 cm apart in a central area 8 cm×8 cm. A polyester film (Melinex (Trade Mark), available from I.C.I.) 25 microns thick was perforated with holes 1.5 mm in diameter. The polyester film was placed over the perforated area of the ethylene-vinyl acetate film on the non-adhesive side so that the perforations were out of register with each other. Hydrophilic polyurethane film was then heat sealed to the ethylene vinyl acetate layer around the polyester film, to form an adhesive dressing. The moisture vapour transmission rate of the dressing was measured using the method described in Example 5 with the following results,

| Time after injection (hr.) | Moisture vapour transmission rate (gm$^{-2}$24 hr$^{-1}$) |
|---|---|
| 0 | 3,450 |
| 1.5 | 2,680 |
| 2 | 2,680 |
| 3 | 2,660 |
| 4 | 2,470 |
| 5.5 | 1,320 |
| 6 | 650 |

The results showed that this dressing was suitable as a wound dressing.

EXAMPLE 11

Preparation of Surgical Dressing

An acrylic adhesive coating was transferred on to one surface of a polyethylene film 22 microns in thickness. The adhesive film was then perforated with holes 1.5 mm in diameter in a central area. A similarly perforated film of polyester was laid over this area but with the holes of each film out of register. A film of hydrophilic polyurethane was heat sealed to the polyethylene film to form an adhesive dressing. The moisture vapour transmission rate was measured by the method described in Example 5 with the following results,

| Time after injection (hr.) | Moisture vapour transmission rate (gm$^{-2}$ 24 hr$^{-1}$) |
| --- | --- |
| 0 | 3,000 |
| 1.5 | 1,510 |
| 2 | 1,130 |
| 4 | 960 |
| 6 | 670 |

The results showed that this dressing was suitable as a dressing for exuding wounds.

EXAMPLE 12

Preparation of Surgical Dressing

A film of a blend of 60 parts linear polyether polyurethane/40 parts high impact polystyrene was formed by extrusion and cold drawn to give a film 75 microns in thickness. An acrylic adhesive layer was transfer coated on to one surface of this film. This adhesive coated film was perforated by slits 0.5 cm in length. A film of polyvinyl alcohol was cast from a 12% aqueous solution. The film was dried at 60° C. The film was then autoclaved to cross-link the polymer. The final thickness of the film was 38 microns. This film was laminated to the perforated film using an acrylic adhesive spread around the periphery of the perforated area. The dressing so formed was measured for moisture vapour transmission rate using the method described in Example 5 with the following results,

| Time after injection (hr.) | Moisture vapour transmission rate (gm$^{-2}$ 24 hr$^{-1}$) |
| --- | --- |
| 0 | 4,080 |
| 1.5 | 1,250 |
| 2 | 770 |
| 3 | 430 |
| 4 | 430 |

The results and visual observation showed that this dressing was suitable for use on exuding wounds.

Description 1

"Dry" MVP Determination

Discs of the material under test were clamped over Payne Permeability Cups (flanged metal cups) using sealing rings and screw clamps. The exposed surface area of the test sample is 10 cm$^2$. Each cup contains approximately 10 ml. of distilled water.

After weighing the cups are placed in a fan assisted electric oven which is maintained at 37±1° C. The relative humidity within the oven is maintained at 10% by placing 1 Kg. of anhydrous 3-8 mesh calcium chloride on the floor of the oven.

The cups are removed after 24 hours, allowed to cool for 20 minutes and re-weighed. The MVP of the test material is calculated from the weight loss and expressed in units of grams of weight per square meter per 24 hours.

"Wet" MVP determination

The method described above is employed except that the Payne Cups are inverted in the oven so that the water within the cups is in contact with the test material. The following results were obtained:

| Material | Thickness ($\mu$m) | MVP (Upright gm$^{-2}$ 24 hr$^{-1}$) | MVP (Inverted gm$^{-2}$ 24 hr$^{-1}$) |
| --- | --- | --- | --- |
| Plasticised regenerated cellulose* | 30 | 4100 | >14000 |
| Hydrophilic Polyurethane (25% water content) | 25-30 | 2700 | >14000 |
| +Polyether-polyamide | 60-80 | 4600 | >14000 |
| Cross-lined polyvinyl alcohol | 50 | 3000 | >14000 |

*Rayophane
+Pebax 4011

Description 2

General Preparative Procedure

The required quantities of polyglycol, chain extenders (aliphatic diol or diamine) and water were warmed to approximately 80° C. and mixed completely in a covered beaker. The required quantity of di-isocyanate was added to the warm mixture and the total mass stirred until a clear solution resulted. The temperature was allowed to fall to 70° C. at which point the appropriate weight of catalyst was added from a syringe and the mixture stirred continuously until exothermic reaction reached 90° C. when it was poured quickly into a polypropylene tray and transferred immediately to an oven to cure for ½ hour at 100° C. The resulting foam was left at room temperature for at least 16 hours before cutting into pieces. (These pieces could be dissolved in a convenient solvent such as dichloromethane, methanol or mixtures thereof to form a solution suitable for casting or coating objects).

Hydrophilic polyurethanes were prepared by the above procedure using polyethylene glycol 1540 (supplied by Union Carbide Corp.), polytetramethylene glycol 1010 (supplied by Quaker Oats Corporation) ethane diol and 4,4'dicyclohexylmethane di-isocyanate (supplied as Hylene W by Du Pont or Desmodur W by Bayer).

The materials also employed 0.25% water and 0.2% di-n-butyltinlaurate solution (Catalyst T-12).

Description 3

Preparation of Hydrophilic Polyurethane

A polyurethane having a potential water content of 85% was prepared from:
Polyethylene glycol (Mol. Wt 6750): 33.5 g (0.05 mole)
Digol: 5.3 g (0.05 mole)
Desmodur W: 56.53 g (0.215 mole)
Catalyst T-12: 0.8 ml The polyethylene glycol and digol were weighed into a beaker (1 liter) and then the beaker was placed in an oven at 90° C. to melt the polyethylene glycol. The di-isocyanate Desmodur W was then added and the mixture stirred until homogenous. The catalyst was added and stirring continued for another minute. The mixture was then poured into a high density polypropylene dish and then placed in the oven at 90° C. for 2 hours to cure. The polyurethane so formed was capable of absorbing water to give a water content of 85% when fully hydrated.

We claim:

1. A moisture vapor permeable adhesive wound dressing which adheres to the skin but not to wounds which comprises an outer film and a body contacting film which outer film comprises a continuous film which has a moisture vapour permeability which is greater when in contact with water than when not in contact with water and which outer film is attached at least around its edges to the body contacting film so as to form a sealed pouch into which exudate may pass from an exuding wound, said body contacting film being substantially coextensive with the outer film and being interrupted in the area within the sealed pouch, and which body contacting film comprises a backing film and a continuous adhesive layer spread over the non-interrupted surface of the body contacting film remote from the outer film suitable for adhering the dressing to the skin but not to the wound, said dressing further having between the outer film and the non-adhesive side of the body contacting film a water transmitting film whereby when the dressing is placed on an exuding wound the wound exudate passes through the body contacting layer into the sealed pouch and contacts the outer film which has a high moisture vapour permeability when in contact with water and thus prevents the dressing from forming a blister when used on an exuding wound.

2. A dressing according to claim 1 in which the water transmitting film is a non-woven fabric.

3. A dressing according to claim 1 in which the continuous film has a moisture vapour permeability of greater than 8000 g/m$^2$/24 hr$^1$ when in contact with water and not greater than 4800 g/m$^2$/24 hr$^1$ when not in contact with water, when measured at 37° C. and 100% to 10% relative humidity.

4. A dressing according to claim 1 in which the continuous film is a hydrophilic polymer capable of containing up to 90% water when hydrated and is 15 to 80 microns in thickness.

5. A dressing according to claim 1 in which the adhesive layer of the body contacting film comprises a polyvinyl ethyl ether adhesive or an acrylate ester copolymer adhesive.

6. A dressing according to claim 1 in which the backing layer of the body contacting film is a polymeric film interrupted by means of slits from 0.3 to 1.4 cm long.

7. A dressing according to claim 1 in which the body contacting film is a polyurethane.

8. A dressing according to claim 1 in which the body contacting film has a thickness of 15 to 100 microns.

9. A dressing according to claim 1 in which the continuous film is heat sealed to the body contacting film.

10. A dressing according to claim 1 in a sterile form packaged in a bacteria proof pack.

11. A dressing according to claim 2 in which the continuous film has a moisture vapor permeability of greater than 8000 g/m$^2$/24 hr$^1$ when in contact with water and not greater than 4800 g/m$^2$/24 hr$^1$ when not in contact with water, when measured at 37° C. and 100% to 10% relative humidity.

12. A dressing according to claim 2 in which the continuous film is a hydrophilic polymer capable of containing up to 90% water when hydrated and is 15 to 80 microns in thickness.

13. A dressing according to claim 2 in which the adhesive layer of the body contacting film comprises a polyvinyl ethyl ether adhesive or an acrylate ester copolymer adhesive.

14. A dressing according to claim 2 in which the body contacting film is a polyurethane.

15. A dressing according to claim 3 in which the continuous film is a hydrophilic polymer capable of containing up to 90% water when hydrated and is 15 to 80 microns in thickness.

16. A dressing according to claim 3 in which the adhesive layer of the body contacting film comprises a polyvinyl ethyl ether adhesive or an acrylate ester copolymer adhesive.

17. A dressing according to claim 3 in which the body contacting film is a polyurethane.

18. A dressing according to claim 4 in which the adhesive layer of the body contacting film comprises a polyvinyl ethyl ether adhesive or an acrylate ester copolymer adhesive.

19. A dressing according to claim 4 in which the body contacting film is a polyurethane.

20. A dressing according to claim 5 in which the body contacting film is a polyurethane.

* * * * *